United States Patent [19]

Selmer et al.

[11] Patent Number: 5,165,912
[45] Date of Patent: Nov. 24, 1992

[54] METHOD FOR THE DETECTION OF FIBRINOLYTIC ACTIVITY

[75] Inventors: Johan Selmer, Farum; Niels Tromholt, Charlottenlund, both of Denmark

[73] Assignee: Novo Nordisk A/S, Denmark

[21] Appl. No.: 569,127

[22] Filed: Aug. 17, 1990

[30] Foreign Application Priority Data

Aug. 18, 1989 [DK] Denmark ............................ 4082/89

[51] Int. Cl.⁵ ...................... A61K 49/02; A61K 49/00
[52] U.S. Cl. ......................................... 424/1.1; 424/9
[58] Field of Search .......................... 424/1.1, 9, 85.91; 530/387, 402

[56] References Cited

FOREIGN PATENT DOCUMENTS

WO85/03231 8/1985 PCT Int'l Appl. .

OTHER PUBLICATIONS

Krohn, K. A. et al., *Sem. Nucl. Med.* 7(3):219–228 (Jul. 1977).
Peters, A. M. et al., *Brit. Med. J.* 293:1525–1527 (13 Dec. 1986).
Paulsma-De Waal, J. H. et al., *NucCompact* 18:284–286 (1987).
Rosebrough, S. F. et al., *Radiology* 156(2):515–517 (1985).
Rosebrough, S. F. et al., *Radiology* 162(2):575–577 (1987).
Knight, L. C. et al., *J. Nucl. Med.* 29:494–502 (1988).
Jung, M. et al., *Eur. J. Nucl. Med.* 14:246 (1988)(Abstr. 143).
Ahonen, A. et al., *Eur. J. Nucl. Med.* 14:309 (1988)(Abstr. 522).
DeGeeter, F. et al., *Eur. J. Nucl. Med.* 14:246 (1988)(Abstr. 144).
Oster, Z. et al., *Am. J. Radiology* 152:253–260 (1989).
Stuttle, A. W. J. et al., *Eur. J. Nucl. Med.* 14:256 (1988)(Abstr. 201).
Som, P. et al., *J. Nucl. Med.* 27(8):1315–1320 (Aug. 1986).
Hnatowich, D. J. et al., *Eur. J. Nucl. Med.* 13:467–473 (1987).
Karonen, S.-L. et al., *J. Nucl. Med.* 29:1194–1199 (1988).
Karonen, S.-L. et al., *Eur. J. Nucl. Med* 14:252 (1988)(Abstr. 180).
Hnatowich, D. J. et al., *Science* 220:613–615 (1983).
Rhodes, B. A. et al., in *Tumor Imaging* (S. W. Burchiel et al., eds.), New York, Mason Pub., pp. 111–123 (1982).
Cerdan, S. et al., *Magnetic Resonance in Medicine* 12:151–163 (1989).
Saccavini, J. C. et al., *Invest. Radiol. Supp.* 1:S292–S293 (1988).
Hnatowich, D. J., *Immun. Methods* 65:147–157 (1983).
De Geeter, F. et al., *Eur. J. Nucl. Med.* 14:270 (1988), (Abstract No. 285).

*Primary Examiner*—John S. Maples
*Attorney, Agent, or Firm*—Sterne, Kessler, Goldstein & Fox

[57] ABSTRACT

A diagnostic reagent for the detection in vivo of increased release of a fibrinolytic enzyme or increased fibrinolytic activity in the human or animal body comprises an antibody reactive with a fibrinolytic enzyme, or a biologically active fragment of the antibody, labelled with a substance which permits the detection in vivo of binding of the antibody to the fibrinolytic enzyme. In one embodiment, increased clearance of the antibody is provided by subsequent administration of the fibrinolytic enzyme with which the antibody is reactive. The fibrinolytic enzyme is preferably t-PA.

17 Claims, 20 Drawing Sheets

FIG. 4A
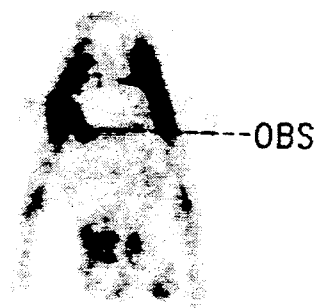
2 1/2 HOUR
FIG. 4B
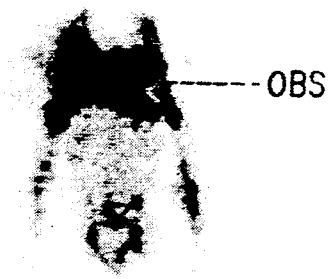
4 HOURS
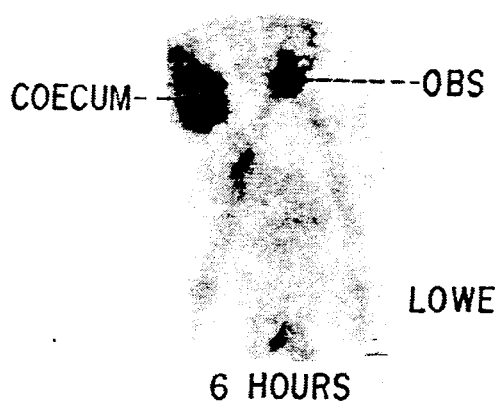
LOWER ABDOMINAL AREA
6 HOURS
FIG. 4C

RIGHT

MURAL THROMBUS IN
AORTIC ANEURYSM

ABDOMEN

FIG. 7A
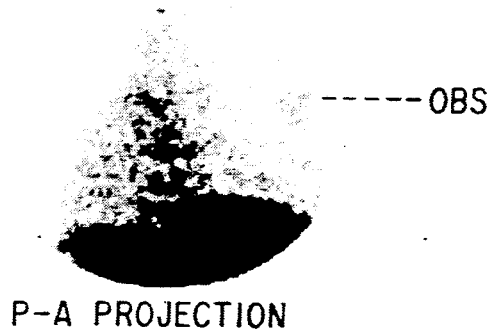
P-A PROJECTION
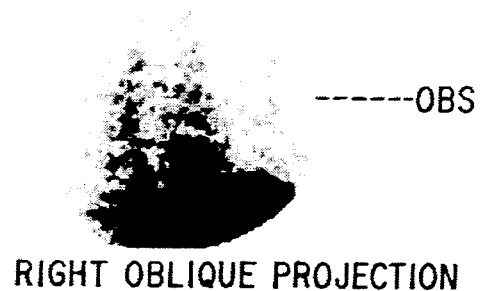
RIGHT OBLIQUE PROJECTION
FIG. 7B

PREOPERATIVE
CRUS

LEFT
---OBS

ONE HOUR AFTER
OPERATION

---OBS

40 HOURS
POSTOPERATIVELY

40 HOURS
POSTOPERATIVELY

POSTERIOR VIEW
24 H.P. I

FIG. 13A
FIG. 13B
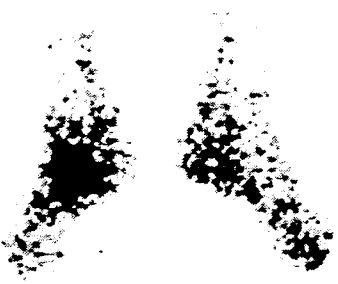
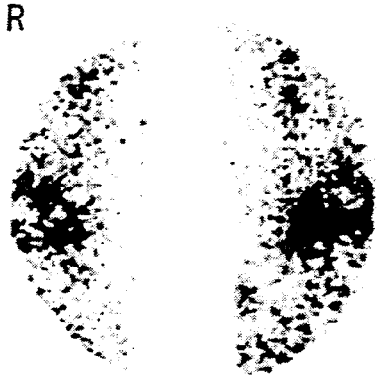
FIG. 13C

RABBITS HEAD

ANTIBODY

ANTERIOR VIEW

RABBITS HEAD

ANTIBODY + T-PA

BEFORE T-PA INJECTION.

CRURAL REGION - ANTERIOR VIEW.

AFTER T-PA INJECTION.

CRURAL REGION - ANTERIOR VIEW.

METHOD FOR THE DETECTION OF FIBRINOLYTIC ACTIVITY

FIELD OF THE INVENTION

The present invention relates to a diagnostic reagent for the detection of the activity of a fibrinolytic enzyme or increased fibrinolytic activity, as well as the use of the reagent in a method of detecting such an enzyme or activity in vivo.

BACKGROUND OF THE INVENTION

The development of a thrombus is a highly complex process. In brief, the attachment of platelets to the vascular surface initiates the entire coagulation cascade, eventually leading to the aggregation of platelets covered with fibrin. The continuing fibrin deposition probably ceases within 24-48 hours from the beginning of the process, after which the thrombus will either be organized, i.e., eventually replaced with fibrous tissue composed of smooth muscle cells or fibroblasts, or fibrinolysis will take place. In the latter case, tissue plasminogen activator is secreted from the endothelium to bind to the fibrin on the thrombus where it catalyses the conversion of plasminogen to plasmin. The thrombus may then disintegrate as a result of fibrinolysis.

With the development of new thrombolytic agents (such as tissue plasminogen activator or streptokinase), rapid, reliable methods of diagnosing thrombosis are needed because there agents are most efficacious within 4-6 hours of thrombus formation (TIMI study group, N. Engl. J. Med. 312:932-936 (1985)). So far, biochemical parameters have not appeared to be of any help in solving this problem (G. E. Austin, Arch. Path. Lab. Med. 111:1158-1162 (1987)).

Scintigraphic methods of diagnosing thrombosis have been suggested. Initially, the reagents developed for the diagnosis were based on radiolabelled blood components (e.g., fibrinogen or platelets), for the reason that these components are incorporated into the thrombi under formation (for a review of these methods, see K. A. Krohn and L. C. Knight. "Radiopharmaceuticals for Thrombosis Detection: Selection, Preparation and Critical Evaluation", Seminars in Nuclear Medicine, Vol. VII, No. 3, July 1977, pp. 219-228). Some disadvantages of using labelled fibrinogen or platelets have been reported. In the case of radiolabelled platelets, A. M. Peters et al., British Medical Journal 293:1525 (Dec. 13, 1986), briefly point out that the production of labelled platelets is time-consuming and requires considerable technical skill for which reason its use has not become widespread. One of the most serious drawbacks is that the accumulation of the reagents in thrombi which are older than about 24 hours is presumably insufficient to permit scintigraphic detection (e.g., as briefly indicated by J. H. Paulsma-De Waal et al., NucCompact 18:284-286 (1987)).

More recently, attempts have been made to employ radiolabelled antibodies against a variety of blood components as reagents for the diagnosis of thrombosis. A considerable number of publications report the use of monoclonal or polyclonal antifibrin antibodies labelled with a variety of radioactive isotopes, $^{111}$In, $^{131}$I or $^{99m}$Tc being the most commonly used isotopes, for the diagnosis of deep venous thrombosis in particular.

Thus, for instance, S. F. Rosebrough et at., Radiology 156:515-517 (1985), describe the use of $^{131}$I labelled monoclonal antifibrin antibodies for the imaging of venous thrombi induced in dogs. S. F. Rosebrough et al., Radiology 62:575-577 (1987), describe the use of $^{131}$I labelled monoclonal antibodies specific for human and dog fibrin for the imaging of mature thrombi, reporting the successful imaging of canine deep venous thrombi 1, 3 and 5 days old. Similarly, L. C. Knight et al., J. Nucl. Med. 29:494-502 (1988), describe the use of an $^{111}$In labelled monoclonal anti-fibrin antibody for imaging vascular thrombi in an animal (rabbit and dog) model, reporting the imaging of thrombi up to 4 days old in five out of eight rabbits, and of 0.5 hour- and 24 hour-old thrombi in six out of eight dogs. All these studies conclude that, based on these findings, labelled monoclonal antifibrin antibodies may also be useful for imaging thrombi in human patients.

Studies of the diagnosis of deep venous thrombosis in human beings by means of radiolabelled monoclonal antifibrin antibodies has been described by, for instance, M. Jung et al., Eur. J. Nucl. Med. 14(5-6):280-283 (1988); H. J. Aronen et al., Eur. J. Nucl. Med. 14(5-6):288-290 (1988); and F. De Geeter et al., Eur. J. Nucl. Med. 14(4-6):284-287 (1988). Jung et al. conclude that the scintigraphical analysis is useful for the diagnosis of established deep venous thrombosis of the calf, popliteal vein and thigh when the thrombi are not older than ten days (M. Jung et al., Eur. J. Nucl. Med. 14(5-6):280-283 (1988)). Aronen et al. report false positive results of the scintigraphic analysis and conclude that it is necessary to confirm a positive result by phlebography (H. J. Aronen et al., Eur. J. Nucl. Med. 14(5-6):288-290 (1988)). De Geeter et al., consider antifibrin scintigraphy to present a promising alternative to contrast venography (F. De Geeter et al., Eur. J. Nucl. Med. 14(5-6):284-287 (1988)).

Antifibrin antibodies have the advantage that their antigenic site is located in the thrombotic area. However, antifibrin antibodies have a long half-life in the circulation and consequently there is a high background activity. This limits the use of labelled antifibrin antibodies to non-emergency situations (cf. Z. Oster and P. Som, American Journal of Radiology 152:253-260 (1989), who also remark that labelled antifibrin antibodies may particularly well suited for the detection of mature deep venous thrombi).

Other publications disclose the use of radiolabelled monoclonal anti-platelet antibodies for the diagnosis of thrombosis. Thus, A. M. Peters et al., British Medical Journal 293:1525-1527 (1986), describe the use of an $^{111}$In labelled monoclonal anti-platelet antibody for imaging deep venous thrombi in patients and conclude that the antibody is useful for imaging fresh thrombi rather than mature thrombi because platelet adherence to the surface of the thrombus will have to be in progress in order to obtain a positive result of the imaging. They also suggest the use of the antibody for imaging renal allograft rejection, platelet uptake on prosthetic arterial surfaces and arterial and intracardiac thrombi.

A. W. J. Stuttle et al., Eur. J. Nucl. Med. 14(5-6):122-125 (1988), report the use of a fragment of a monoclonal antiplatelet antibody for imaging deep venous thrombi. Similarly, P. Som et al., J. Nucl. Med. 27:1315-1320 (1987), describe the use of $^{99m}$Tc labelled monoclonal antiplatelet antibody fragments for imaging experimentally induced thrombi in dogs. They conclude that the antibody fragments can be used for imaging thrombi in the thorax without blood-pool subtraction, and that they may be useful for detecting intracoronary thrombi. They further indicate that the labelling of the antibody fragments is simpler than labelling platelets.

Z. H. Oster and P. Som. *American Journal of Radiology* 152:253-260 (February 1989), discuss the properties of labelled antiplatelet antibodies versus labelled antifibrin antibodies for the purpose of thrombus imaging. Relative to antifibrin antibodies which, as discussed above, have a long half-life, antiplatelet antibodies have the advantage of a rapid blood clearance. Their antigenic site is located on the circulating platelets, giving these the opportunity to be incorporated into the developing thrombus at an early stage, thereby increasing the target/blood ratio (i.e., the ratio between the activity at the thrombotic site and the background activity in the blood). On the other hand, the attachment of the antiplatelet antibodies to circulating platelets makes it difficult to visualize thrombi which are older than about 24 hours.

The utility of radiolabelled fibrinolytic enzymes (e.g., tissue plasminogen activator (t-PA), urokinase, streptokinase) or precursors therefor (e.g., plasminogen) for the detection of thrombi as well as for the localization of malignant tumors (in the case of t-PA) has also been studied for the reason of their affinity to fibrin or other components of thrombi. Thus, J. H. Paulsma-De Waal et al., op. cit., describe the study of Tc-labelled t-PA as a reagent for the detection of thrombosis. They conclude that systemically injected radiolabelled t-PA yields no useful results (i.e., activity uptake in the thrombus), presumably because of its rapid clearance in the liver, whereas locally injected labelled t-PA shows a distinct uptake of activity in the thrombus. On the other hand, D. J. Hnatowich et al., *Eur. J. Nucl. Med.* 13:467-473 (1987), have found positive imaging of experimentally induced canine thrombi with intravenously injected recombinant t-PA coupled to diethylenetriaminepentaacetic acid labelled with $^{111}$In, while still observing a rapid clearance of their reagent in the liver.

S. -L. Karonen et al., *J. Nucl. Med.* 29:1194-1199 (1988), report the localization of malignant tumors with radiolabelled recombinant t-PA, concluding that the accumulation of labelled t-PA in malignant tissue points to a potential use of the labelled t-PA for the detection of tumors. However, a later study (S. -L. Karonen et al., *Eur. J. Nucl. Med.* 14(5-6):610-611 (1988)) confirms that a major proportion of the radiolabelled t-PA is eliminated rapidly from plasma. Another disadvantage of using labelled t-PA is that because it accumulates in the liver, the risk of obtaining too high a local radioactive dosage makes it necessary to reduce the amount of diagnostic reagent employed. Apart from this, the labelled t-PA has to comprise with the t-PA formed by the body as a response to fibrin deposition for attachment sites on the thrombus.

Labelled streptokinase and urokinase have also been used for thrombus imaging, as reviewed by K. A. Krohn and L. C. Knight, op. cit., who also report some of the difficulties inherent in using either of these enzymes (vide p. 226) and conclude that they are not yet clinically useful for the localization of thrombi. The use of radiolabelled plasminogen has also been reviewed by K. A. Krohn and L. C. Knight, op. cit., who conclude that it is of potential use for imaging older thrombi.

SUMMARY OF THE INVENTION

Recognizing the potential importance of detecting and diagnosing thrombotic events and cognizant of the need for highly efficient in vivo detection methods, the inventors have evaluated new strategies to overcome the limitations of the current technology.

These studies have culminated with the development of a diagnostic reagent for the detection, in vivo, of the release of a fibrinolytic enzyme. These studies have further culminated with the development of a diagnostic reagent for the detection, in vivo, of fibrinolytic activity.

According to the invention, there is first provided an antibody reactive with a fibrinolytic enzyme, such antibody permitting the detection, in vivo, of binding of such antibody to a fibrinolytic enzyme, in the human or animal body.

According to the invention, there is further provided a diagnostic reagent for the in vivo detection of the release of a fibrinolytic enzyme in the human or animal body, such reagent comprising an antibody reactive with a fibrinolytic enzyme, wherein such antibody is labelled with a substance which permits the detection, in vivo, of binding of such antibody to such fibrinolytic enzyme.

According to the invention, there is further provided a diagnostic reagent for the in vivo detection of increased fibrinolytic activity in the human or animal body, such reagent comprising an antibody reactive with a fibrinolytic enzyme, where such antibody is labelled with a substance which permits the detection, in vivo, of binding of such antibody to such fibrinolytic enzyme.

According to the invention, there is further provided a diagnostic composition, such diagnostic composition comprising (1) an antibody reactive with a fibrinolytic enzyme, such antibody being labelled with a substance which permits in vivo detection of binding of the antibody to such fibrinolytic enzyme, and (2) a fibrinolytic enzyme with which such antibody is reactive.

According to the invention, there is further provided a method for the in vivo detection of an increased release of a fibrinolytic enzyme in the human or animal body.

According to the invention, there is further provided a method of in vivo detection of an increased release of a fibrinolytic enzyme in the human or animal body, such method comprising (1) administering, to a human or animal subject, a diagnostically effective amount of an antibody reactive with a fibrinolytic enzyme, such antibody being labelled with a substance permitting the in vivo detection of binding of such antibody to such fibrinolytic enzyme, and (2) localizing increased release of a fibrinolytic enzyme in the subject by determining the presence of such bound labelled antibody.

According to the invention, there is further provided a method for the in vivo detection of an increased fibrinolytic activity in the human or animal body.

According to the invention, there is further provided a method of in vivo detection of increased fibrinolytic activity in the human or animal body, the method comprising (1) administering, to a human or animal subject, a diagnostically effective amount of an antibody reactive with a fibrinolytic enzyme, which antibody being labelled with a substance permitting the in vivo detection of binding of such antibody to such fibrinolytic enzyme, and (2) localizing increased fibrinolytic activity in such subject by determining the presence of such bound labelled antibody.

According to the invention there is further provided a method of using an antibody, wherein such antibody is reactive with a fibrinolytic enzyme, and wherein such antibody is used for the preparation of a diagnostic reagent for the in vivo detection of an increased release of a fibrinolytic enzyme in the human or animal body.

According to the invention there is further provided a method of using an antibody, wherein such antibody is reactive with a fibrinolytic enzyme, and wherein such antibody is used for the preparation of a diagnostic reagent for the in vivo detection of increased fibrinolytic activity in the human or animal body.

BRIEF DESCRIPTION OF THE DRAWINGS

FIG. 4 is a scintigram showing increased uptake of $^{111}$In-labelled t-PA MoAb at the site of gastrointestinal bleeding in the lower, control part of the abdomen and cecum.

FIG. 7 is a scintigram showing increased uptake of $^{111}$In-labelled t-PA MoAb in an area of pulmonary embolism.

FIG. 13 is a three scintigrams showing increased uptake of $^{111}$In-labelled t-PA MoAb corresponding to rheumatoid arthritis of the joints in the wrists, right ankle and knees.

DETAILED DESCRIPTION OF THE INVENTION

I. Definitions

Figure 1:
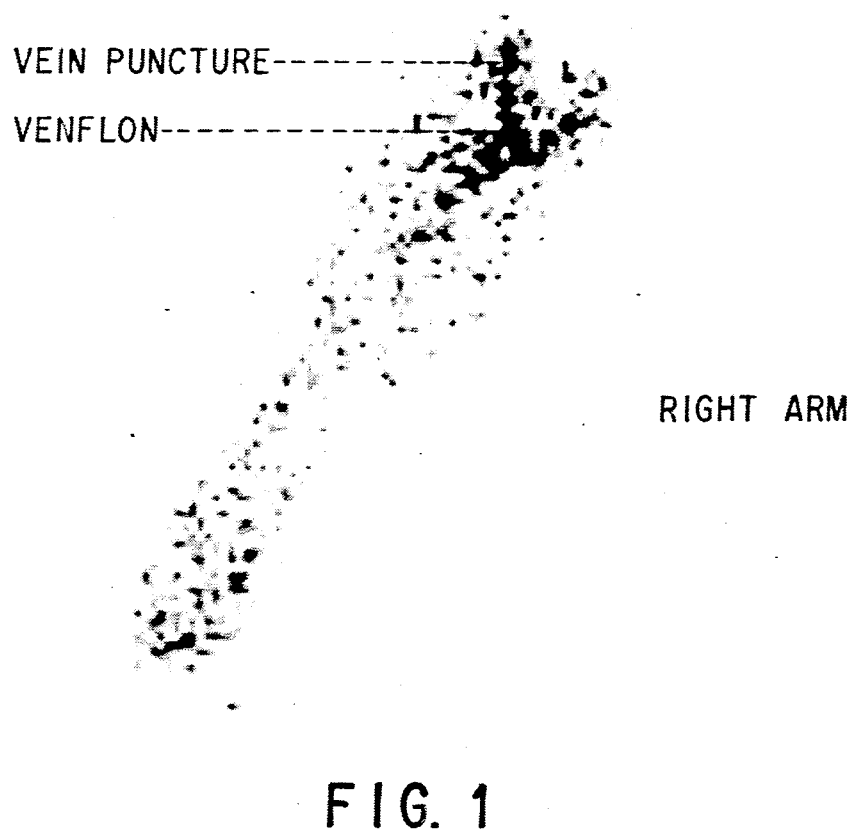
FIG. 1 is a scintigram showing increased uptake of $^{111}$In-labelled monoclonal anti-t-PA antibody (t-PA MoAb) at the site of blood sampling in the cubital vein.

In the description that follows, a number of terms used in immunology and protein technology are extensively utilized. In order to provide a clear and consistent understanding of the specification and claims, including the scope to be given such terms, the following definitions are provided.

Administered

As used herein, the term "administered" is intended to mean any method of delivering a desired substance into a human or other animal, such as, for example, parenteral (intravenous, intramuscular), nasal, enteral (oral) or rectal (enema, suppository) administration.

Fibrinolytic Enzyme

As used herein, in the present context, the term "fibrinolytic enzyme" is understood to mean an enzyme which either (1) directly catalyses the degradation of fibrin (e.g., plasmin) or a precursor therefor (e.g., plasminogen). or (2) catalyses the cleavage of an enzyme precursor into a fibrinolytically active form (for example, t-PA or urokinase).

As used herein, the term "fibrinolytic enzyme" is meant to include both the native fibrinolytic enzyme and biologically active derivatives of the fibrinolytic enzyme. Preferred fibrinolytic enzymes are those which shown an affinity for fibrin, i.e., which adhere to fibrin itself or to a component adhering to fibrin (for example t-PA, plasmin, plasminogen) or those which have been modified to shown an affinity for fibrin (for example, modified urokinase).

As used herein, the expression "increased fibrinolytic activity" is intended to mean a higher than normal level of fibrin degradation. As used herein, the term "increased release of a fibrinolytic enzyme" refers to the increased secretion of one or more enzymes which form part of the fibrinolytic system, for instance in connection with a weakly ischaemic condition in which no fibrin deposition and consequently no fibrinolysis takes place. By "normal" is meant a value which is considered to be average for a physiological status, such as, for example, for a certain species, age and gender.

Antibody

The term "antibody" is intended to be synonymous with "immunoglobulin" and is meant to refer to any protein which possesses a biological activity which allows it to recognize and react with an antigen. As used herein, the term "antibody" is meant to include both the native antibody and biologically active derivatives of such antibody. Unless specified otherwise, "antibody" refers specifically to an antibody which is reactive with a fibrinolytic enzyme.

By "react with" an antigen is meant that such antibody possesses an affinity for such an affinity results in the formation of a non-covalent, protein-protein complex between such antibody and antigen. As used herein, the term antibody subunit refers to a protein which contains the amino acid sequence of a light or heavy chain of such an antibody, or a biologically active fragment thereof, such light or heavy chains or biologically active fragments thereof being capable of being modified (for example, by reassociation with another immunoglobulin) to reveal their inherent immunological activity.

Biologically Active Derivative

A "biologically active derivative" of a protein, such as an antibody or enzyme, is a protein which possesses a biological property (either functional or structural) that is substantially similar to a biological activity of a native protein but which may or may not be identical to the native protein. A biologically active derivative of a protein may or may not contain post-translational modifications, such as covalently linked carbohydrate, depending on the necessity of such modifications for the performance of a specific function. The term "biologically active derivative" is intended to include biologically active "fragments," "variants," "chemical derivatives" and "analogues" of a protein.

As used herein, a protein may be said to be a "chemical derivative" of another protein when it contains additional chemical moieties not normally a part of the molecule. Such moieties include labels, and especially radiolabels, which allow the presence of the protein to be detected. Such moieties may improve the molecule's solubility, absorption, biological half life, etc. The moieties may alternatively decrease the toxicity of the molecule, eliminate or attenuate any undesirable side effect of the molecule, etc. Moieties capable of mediating such effects are disclosed in *Remington's Pharmaceutical Sciences* (1980). Procedures for coupling such moieties to a molecule are well known in the art.

Analogue

As used herein, the term "analogue" is meant to include derivatives of a protein, (for example, derivatives of a fibrinolytic enzyme of the invention or derivatives of an antibody of the invention), which are obtained by modifying or mutating the DNA sequence encoding such protein in a manner resulting in addition, substitution, insertion or deletion of one or more amino acids in the native sequence, or, in a manner which does not change the amino acid sequence but wherein the DNA coding sequence differs from that found in a naturally produced protein.

The term "analogue" is also meant to include an enzyme homologous to an enzyme of the invention or an enzyme which is reactive with an antibody raised or directed against a native enzyme of the invention. It should be noted that, for t-PA at least, several such analogues have previously been described and are known in the art.

Fragment

A "fragment" of a protein is meant to refer to a protein which contains a portion of the complete amino acid sequence of the native protein. If the protein contains more than one peptide subunit, then, as used herein, the term "fragment" includes at least three meanings: (1) a full-length peptide which is one subunit of the native multi-subunit protein, (2) a peptide subunit of the native protein which contains fewer amino acids than the native subunit, and (3) a multisubunit protein which contains one or more subunits which contain fewer amino acids than the native subunit(s), for example, an Fab fragment. One of ordinary skill in the art would understand which meaning to give the word "fragment" as used herein from the properties of the native protein.

Therefore, in accordance with conventional practice, a "fragment of an antibody" may be a Fab', F(ab')$_2$ or Fv fragment of the antibody as well as a single-domain antibody.

By a "biologically active fragment" of an antibody is meant a fragment of an antibody which retains all or some of the biological activity possessed by the antibody. For example, if the fragment contains the antigen binding domain(s) of an antibody, then such fragment is said to be a biologically active fragment if such fragment also possesses the ability to recognize and react with antigens at those domains.

Variant

A "variant" of a protein is meant to refer to a protein substantially similar in structure and biological activity to either the native protein or to a fragment thereof, but not identical to such molecule or fragment thereof. A variant is not necessarily derived from the native molecule. The term "variant" is intended to include genetic alleles. Thus, provided that two proteins possess a similar structure and biological activity, they are considered variants as that term is used herein even if the composition or secondary, tertiary, or quaternary structure of one of the proteins is not identical to that found in the other.

II. The Preparation and Methods of the Invention

Despite the existence of a wide variety of radiolabelled reagents suggested for the detection of thrombi, it is, however, believed to be novel to label an antibody against a fibrinolytic enzyme and use the labelled antibody for the detection in vivo of increased fibrinolytic activity. The research data obtained so far on these reagents indicate that their use overcomes at least some of the deficiencies reported for the known reagents.

Accordingly, the present invention relates to a diagnostic reagent for the detection in vivo of increased release of a fibrinolytic enzyme or increased fibrinolytic activity in the human or animal body, the reagent comprising an antibody reactive with a fibrinolytic enzyme, or a fragment of said antibody, labelled with a substance which permits the detection, in vivo, of binding of the antibody to the fibrinolytic enzyme.

The modifications needed to obtain a fibrinolytic enzyme with affinity for fibrin from an enzyme with low fibrin affinity (e.g., native urokinase) may be produced by recombinant DNA techniques in a manner known per se (Maniatis, T. et al., *Molecular Cloning (A Laboratory Manual)*, Cold Spring Harbor Laboratory, 2nd edition, 1989). Of course, such analogues or modified enzymes are not found in the human or animal body in nature, but may form part of a particular embodiment of the present diagnostic method whereby an analogue or a modified enzyme is administered to the patient prior to or after the administration of the labelled antibody. One advantage of such a method would be that the level of fibrinolytic enzyme at the site of, e.g., a thrombus or other fibrin deposit may be increased almost at will resulting in increased antibody attachment so as to improve the accuracy of the diagnosis.

Under physiological conditions, the amount of circulating fibrinolytic enzymes is low, whereas the local concentration of these enzymes in case of thrombosis is greatly increased which means that the antigenic sites for antibodies against any one of the fibrinolytic enzymes in question are found almost exclusively in the thrombotic area, resulting in a favorable target/blood ratio. This may be further enhanced by administering the fibrinolytic enzyme with which the antibody is reactive before or after administering the antibody. In this way, it is possible to increase the level of the fibrinolytic enzyme in question on older thrombotic lesions and to remove non-bound antibodies against the fibrinolytic enzyme so as to reduce the background activity in the case of acute investigations.

In a particularly favored embodiment, the fibrinolytic enzyme is t-PA which, on administration, is cleared rapidly from the circulation, being bound to a hepatic receptor. It has surprisingly been found that when t-PA or an analogue thereof as defined above is administered at some suitable point after administration of an anti-t-PA antibody, the resulting t-PA/anti-t-PA complex has a far shorter half-life in plasma than the uncomplexed antibody due to the binding of the complex to the same receptor as free t-PA.

Consequently, according to this embodiment, the invention further relates to a diagnostic composition which comprises a kit, such kit providing, in separate containers,
(a) an antibody reactive with a fibrinolytic enzyme, in particular t-PA, or a biologically active derivative of said antibody, labelled with a substance which permits detection in vivo of binding of the antibody to the fibrinolytic enzyme, and
(b) a fibrinolytic enzyme with which the antibody is reactive, in particular t-PA of an analogue thereof.

In another aspect, the present invention relates to a method of in vivo detection of increased release of a fibrinolytic enzyme or increased fibrinolytic activity in the human or animal body, the method comprising
(a) administering, to a human or animal patient, a diagnositically effective amount of an antibody reactive with a fibrinolytic enzyme, or a biologically active derivative of said antibody, labelled with a substance permitting the detection in vivo of binding of the antibody or biologically active derivative thereof to the fibrinolytic enzyme, and
(b) localizing increased release of a fibrinolytic enzyme or increased fibrinolytic activity in the patient by determining the presence of bound labelled antibody.

In one embodiment of this method, an analogue of a fibrinolytic enzyme or an enzyme which has been modified to exhibit fibrin affinity may be administered to the patient prior to the administration of the labelled antibody. As indicated above, this may ensure a higher concentration of the enzyme at the site of the fibrin deposit and hence a stronger scintigraphic signal (relative to the background activity) permitting a more accurate diagnosis of the condition. Alternatively, the fibrinolytic enzyme or an analogue thereof may be administered at some suitable point after administration of the antibody, as indicated above. Thus, administration of the fibrinolytic enzyme may take place after a period of time sufficient to ensure binding of an adequate amount of the labelled antibody at the site of increased fibrinolytic activity, the subsequent administration of the fibrinolytic enzyme providing for rapid elimination of the antibody remaining in the circulation and consequently for a substantially reduced background activity. This period of time may suitably be from about 30 minutes to about 24 hours. The dosage of the fibrinolytic enzyme is typically below a therapeutic dosage.

In a further aspect, the invention relates to the use of an antibody reactive with a fibrinolytic enzyme, or a biologically active derivative of said antibody, labelled with a substance permitting the detection in vivo of binding of the antibody or biologically active derivative thereof to the fibrinolytic enzyme, for the preparation of a diagnostic reagent for the detection in vivo of increased release of a fibrinolytic enzyme or increased fibrinolytic activity in the human or animal body. As explained above, the fibrinolytic enzyme is preferably selected from the group consisting of t-PA, plasmin, plasminogen, or an analogue thereof, or a modified fibrinolytic enzyme with affinity for fibrin.

A particularly preferred fibrinolytic enzyme for raising antibodies for the present purpose is t-PA or an analogue thereof, in particular native t-PA, as this enzyme exhibits a high affinity for fibrin. Also, the amount of t-PA in blood is normally very small, whereas the concentration of t-PA is high in connection with pathological processes.

Antibodies used in the diagnostic method of the invention are preferably monospecific antibodies directed against a specific component only, in this case the desired fibrinolytic enzyme. Monospecific antibodies may be both polyclonal and monoclonal.

Polyclonal antibodies may be prepared by injecting a suitable animal with a substantially pure preparation of the fibrinolytic enzyme in question (in order to ensure their monospecificity) followed by one or more booster injections at suitable intervals (e.g., from two weeks to a month) up to six months before the first bleeding. Then, while continuing this immunization regimen, the animal is bled about one week after each booster immunization, and antibodies are isolated from the serum in a manner known per se, such as described by Harboe and Ingild, *Scand. J. Immun.* 2 (Suppl. 1):161-164 (1973).

It is, however, preferred to employ monoclonal antibodies (or biologically active derivatives thereof such as Fab', F(ab')$_2$ or Fv fragments) in the method of the invention as this ensures a higher specificity and accuracy of the diagnosis. Monoclonal antibodies may be obtained by well-established methods, e.g., as described by L. C. Petersen et al., *Thrombosis and Haemostasis* 57 (2):205-211 (1987). It should be noted that the monoclonal antibodies may be from any suitable source, and may thus be selected from, for instance, murine or human monoclonal antibodies.

The antibody may also be produced by cloning a DNA sequence coding for the antibody or a biologically active derivative thereof into suitable cell, e.g., a microbial, plant, animal or human cell, and culturing the cell under conditions conducive to the production of the antibody or biologically active derivative in question and recovering the antibody or biologically active derivative thereof from the culture. Possible strategies for the preparation of cloned antibodies or biologically active derivatives of antibodies are discussed in, e.g., L. Riechmann et al., *Nature* 332:323 ff (Mar. 24, 1988), describing the preparation of chimeric antibodies of rat variable regions and human constant regions; M. Better et al., *Science* 240:1041 ff (May 20, 1988), describing the preparation of chimeric mouse-human Fab fragments; A. Sharra and A. Plückthun, *Science* 240:1038–1040 (May 20, 1988), describing the cloning of an immunoglobulin Fv fragment containing antigen-binding variable domains; and E. S. Ward et al., *Nature* 341:544–546 (Oct. 12, 1989), describing the cloning of isolated antigen-binding variable domains ("single domain antibodies").

A particularly preferred antibody for use as a diagnostic reagent for the present purpose is a monoclonal antibody or biologically active derivative thereof reactive with native t-PA or an analogue thereof (as defined above). Monoclonal antibodies against t-PA have been described previously for other purposes, vide for instance L. C. Petersen et al., op. cit., EP 298 783, K. Kaltoft et al., *Proc. Natl. Acad. Sci. U.S.A.* 79:3720–3723 (1982), L. S. Nielsen et al., *The EMBO Journal* 2:115–119 (1983), L. S. Nielsen et al., *Biochemistry* 21:6410–6415 (1982), K. Danø et al., *J. Histochem. Cytochem.* 30:1165–1170 (1982).

The antibodies used in the reagent of the invention should preferably be in substantially pure form in order to improve the accuracy of the diagnosis.

The substance used to label the antibody may suitably be a radioactive isotope. The isotope is preferably one which has a reasonably short half-life so that patients to whom the reagent of the invention is administered do not receive too high a radioactive dosage. The overall radioactive dosage may also be minimized by selecting an antibody which is eliminated from the body within a relatively brief period of time. The isotope may be selected from the ones previously suggested for this purpose, e.g. $^{111}$In, $^{99m}$Tc, $^{131}$I, $^{123}$I or $^{125}$I. Labelling of the antibody with the radionuclide may be performed as described in the art for the radiolabelling of antibodies in general, cf. for instance D. J. Hnatowich et al., *Science* 220:613–615 (1983) (wherein the antibody is conjugated to diethylene triamine pentaacetic acid prior to labelling to facilitate stable binding of the radionuclide), or B. A. Rhodes et al., in *Tumor Imaging* (S. W. Burchiel and B. A. Rhodes eds.), New York, Mason Publishing, pp. 111–123 (wherein the antibody is incubated directly with the radionuclide). Labelling with $^{99m}$Tc in particular may be carried out substantially as described in EP 169,232, EP 271,806 or EP 304,780. The radioactivity emitted by these radioactive isotopes may be measured in a gamma-counter or scintillation camera in a manner known per se.

Alternatively, the substance used to label the antibody may be a substance useful for magnetic resonance imaging. Examples of suitable substances are magnetite particles which may be coated with the antibody and used for imaging substantially as described in S. Cerdan et al., *Magnetic Resonance in Medicine* 12:151–163 (1989), or paramagnetic atoms, e.g. $^{13}$C or gadolinium (cf., for instance, J. C. Saccavini et al., *Invest. Radiol. Suppl.* 1, pp. S292–S293 (1988).

The diagnostic reagent of the invention may be formulated in any manner which makes it suitable for parenteral, nasal, enteric or rectal administration. Thus, the reagent may be in the form of, for instance, an injectable formulation, aerosol formulation, suspension, solution, enema, etc. The reagent may be formulated with pharmaceutically acceptable excipients or vehicles, e.g., isotonic saline, in accordance with conventional pharmaceutical practice. The dosage level of the reagent will usually be in the range of 0.1–10 mg, preferably 0.5–5 mg, e.g., about 1 mg, of the labelled antibody.

It is contemplated that the diagnostic reagent of the invention may be suitable for diagnosing any condition involving a local accumulation of fibrin resulting in locally increased fibrinolytic activity. Thus, the reagent may be useful for diagnosing such conditions as thrombosis (including deep venous thrombosis, coronary thrombosis, cerebral thrombosis, cardiac thrombosis, mural thrombosis, gastrointestinal thrombosis, artherial thrombosis), embolism (including pulmonary embolism), hemorrhage (including cerebral hemorrhage, postoperative hemorrhage, gastrointestinal hemorrhage, hematuria, hemoptysis), gastric or duodenal ulcers, ischemia, neoplasms (including breast cancer, ovarian cancer, malignant melanoma, or brain or bone tumors), vasculitis, local infections, local inflammatory conditions (including arthritis) or fractures.

The following examples are merely intended to illustrate the present invention and not in any way to limit its scope.

EXAMPLES

Example 1

Production of a Monoclonal Antibody Against t-PA a. Purification of t-PA Antigen

The t-PA for the immunization of mice was purified as disclosed in Rijken, D. C. and Collen, D., *J. Biol. Chem.* 256:7035–41 (1981). The purified material contained >95% pure t-PA as determined by silver-stained SDS-polyacrylamide gel electrophoresis.

b. Immunization of AKR Mice with t-PA

Purified t-PA obtained as described above was dialyzed against 0.15M NaCl containing 0.01% (v/v) Tween 80, and the concentration was adjusted to 10 µg/ml.

AKR mice were immunized 3 times at bi-weekly intervals. For the first two immunizations, each mouse was injected subcutaneously with 50 µl t-PA emulsified with 50 µl of Freund's incomplete adjuvant (corresponding to 5 µg of tPA/mouse. The last immunization was identical to the first two, but was given intraperitoneally rather than subcutaneously. Two months later a mouse received an intravenous booster injection of 90 µl t-PA without any Freund's adjuvant.

c. Cell Fusion and Culture of Cells

Three days after the intravenous t-PA booster, the spleen was removed, and a spleen cell suspension was prepared by carefully dissecting and disrupting the spleen. The resulting spleen cells were used for cell fusions as described in Petersen, L. C., et al., *Thrombosis and Haemostasis* 57(2):205–211 (1987). In brief, spleen cells were fused with X63-Ag8-6.5.3 myeloma cells in the presence of a polyethylene glycol solution. After fusion the cells were seeded in 10 96-well microtiter cell plates. Hybridoma supernatants were screened after two weeks growth by enzyme-linked immunosorbent assay using t-PA as the antigen. A positive clone was recloned several times by the technique of limiting dilution to ensure monoclonality. The cell line was then grown on a large scale in "cell factories" from NUNC in a medium consisting of RPMI 1640 (Gibco, UK) with 2% BMS (Gibco, UK).

d. Purification of the Monoclonal Antibody

The hybridoma supernatants were concentrated and the pH was adjusted to 8.3, after which the monoclonal antibody was purified at 4° C. by adsorption to one a Protein A gel. Elution was performed with a citrate buffer pH 4.5.

e. Production of F(ab)$_2$ Fragments

The purified monoclonal antibody (subclass IgG$_1$) was digested with pepsin at a enzyme/substrate ratio of 1:100 at pH 4.30 for 16 h at 37° C. The reaction was stopped by adjusting the pH of the reaction mixture to pH 8.5 with solid Tris. The F(ab)$_2$ was separated from undigested IgG and low molecular weight products on a Ultrogel AcA 44 column. Purification of the antibody, pepsin digestion and purification of F(ab)$_2$ was monitored on silver-stained SDS-gels.

f. Labelling of F(ab)$_2$ with Indium

The purified F(ab)$_2$ was labelled with indium essentially according to the method of Hnatowich (*J. Immun. Methods* 65:147–157 (1983)). Immunoreactivity of conjugates was confirmed by ELISA and with immunosorbent techniques using tPA as antigen. Radiochemical purity was confirmed by HPLC.

Example 2

Case Stories

All patients were injected with 1 mg of the $^{111}$In-labelled anti-t-PA MoAb prepared as described in Example 1 at a radioactive dosage of 100 MBq, except for case B where the radioactive dosage was 50 MBq. Scintigraphic examination was carried out by means of a GE StarCam scintigraphic camera connected to a Star System 2 computer, commencing immediately upon injection of the antibody. No complications were observed for the entire period during which examination took place.

Case "A"

A blood sample was taken from a 50 year-old man from the right cubital vein 3 hours before injection of the labelled antibody. For the first eight hours of the scintigraphic examination, a small venous catheter was placed more distally in the right cubital vein for the purpose of blood sampling. An increased uptake of the labelled antibody at the sites of sampling, was observed on the scintigram 24 hours after injection of the antibody (FIG. 1), indicating that the labelled antibody may be employed for detecting areas of vascular lesions.

Case "B"

Figure 2:
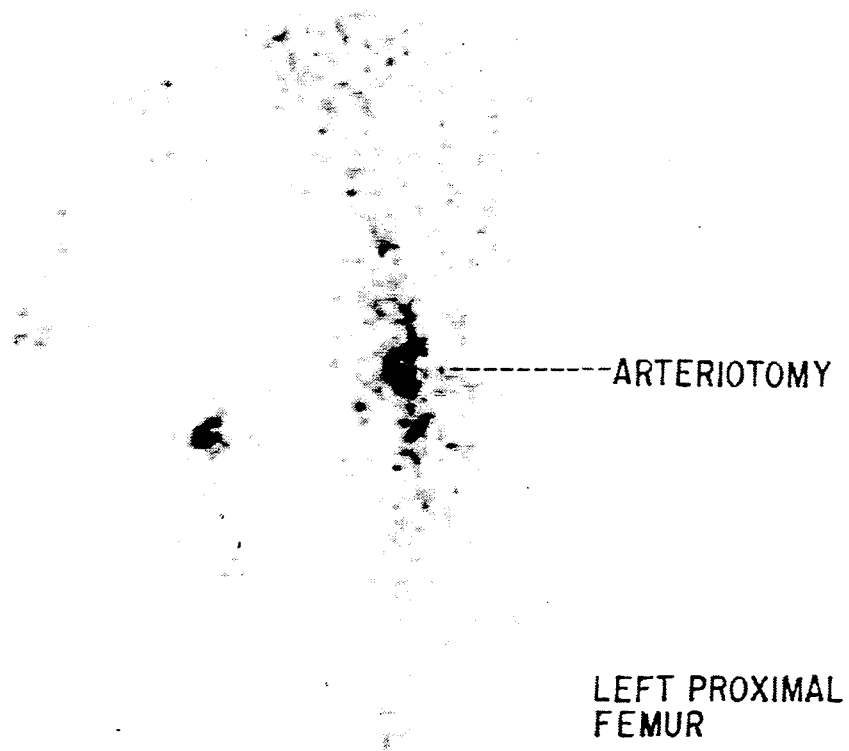
FIGS. 2 and 3 are scintigrams showing increased uptake of $^{111}$In-labelled t-PA MoAb at the site of an arteriotomy in the femoral artery, immediately after injection of the regent (FIG. 2) and after 24 hours (FIG. 3).
Figure 3:
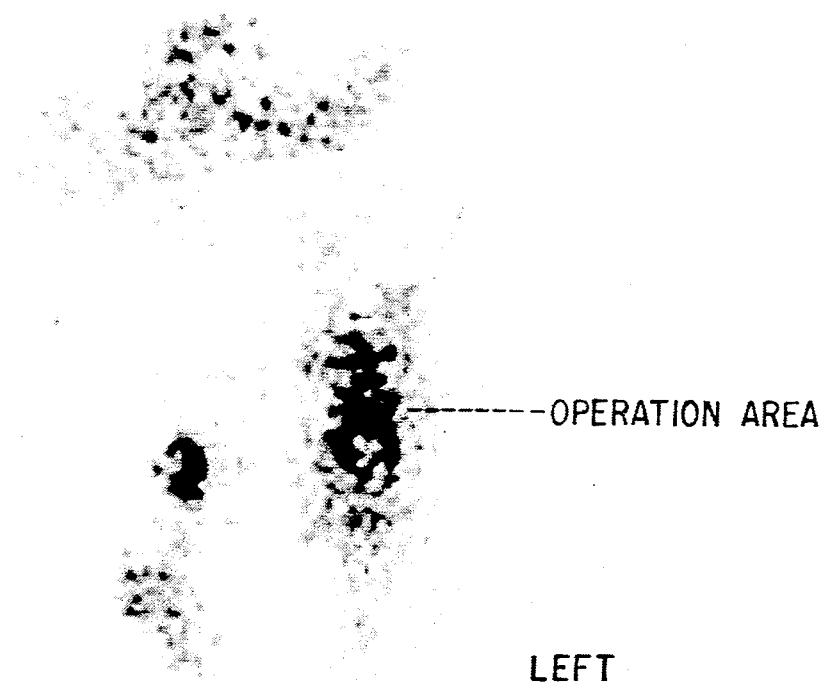

A thromboendarterectomy was performed in the left arteria femoralis communis of a 50 year-old man with severe arteriosclerosis through a 5 cm long arteriotomy. 20 hours later, the labelled antibody was injected. On scintigraphic examination, an instantaneously increased uptake of the antibody was observed along the arteriotomy (FIG. 2). 24 hours after injection, an increased uptake of the antibody was observed in the entire area of operation corresponding to microthrombosis of blood vessels injured in the operation (FIG. 3).

Case "C"

A 61 year-old man had been admitted to hospital several times over the last two years because of severe gastrointestinal bleeding. In spite of careful search for the site of the hemorrhage, this was not found. The patient was admitted again after 5 days of bleeding which continued after his admission to the hospital. Labelled anti-t-PA MoAb was injected, and 2.5 hours later an area with increased fibrinolytic activity was detected in the lower, central part of the abdomen (FIG. 4). The fibrinolytic activity continued to increase in this area, and after 6 hours of scintigraphic examination, activity was detected in the cecum as well. At this point, focally increased activity was still detectable in the area originally observed. On operating the patient, a carcinoid polypus was observed and resected 50 cm from the ileocecal area, i.e., where the increased focal activity had been detected. No gastrointestinal bleeding has been observed since then.

Case "D"

Figure 5:
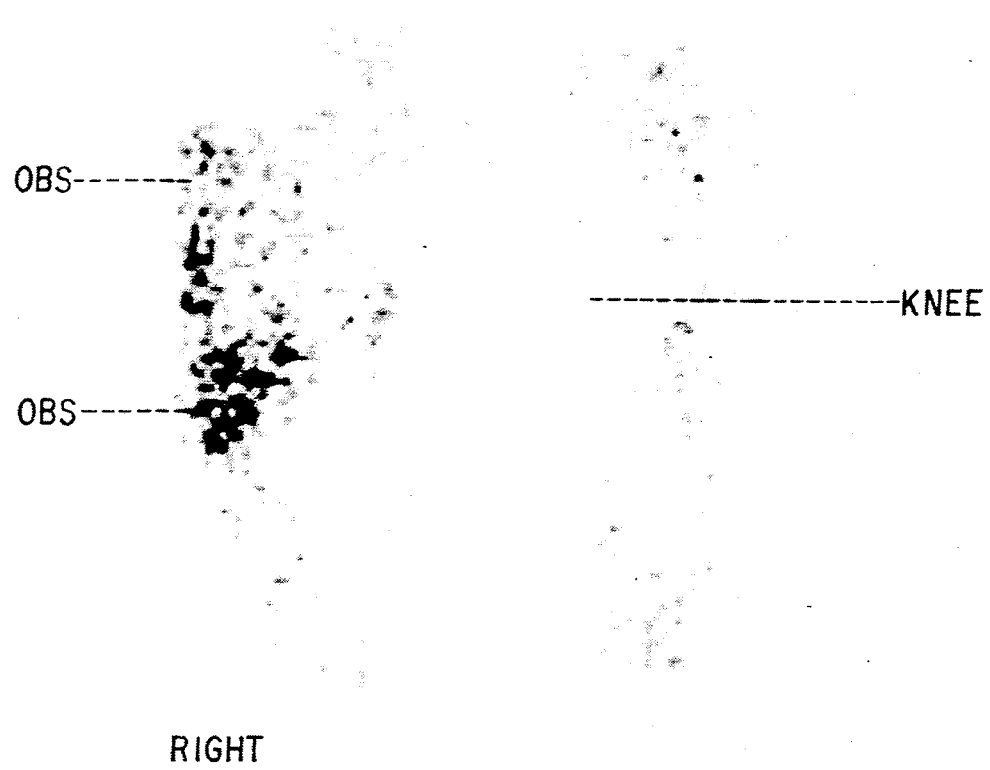
FIG. 5 is a scintigram showing increased uptake of $^{111}$In-labelled t-PA MoAb at areas of deep vein thrombosis at the right knee region.

The patient was a 78 year-old man who had been involved in a traffic accident two weeks prior to the scintigraphic examination. He was immobilized for the entire period because of pain in the back. He was subjected to contrast phlebography on the day before the scintigraphic examination. Examination 20 hours after injection of the labelled antibody showed greatly increased fibrinolytic activity in the right leg (FIG. 5), exactly matching the proximal parts of the occluded thrombotic areas observed by phlebography, i.e., the lateral veins distal to the knee and the distal part of the vena femoralis immediately above the knee.

Case "E"

Figure 6:
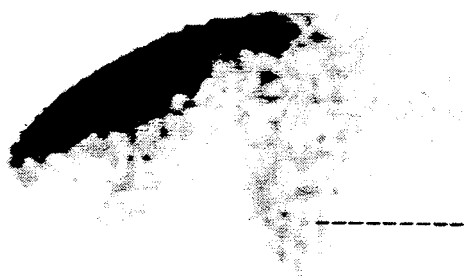
FIG. 6 is a scintigram showing increased uptake of $^{111}$In-labelled t-PA MoAb in the mural thrombus of an abdominal aorta aneurism.
Figure 8A:
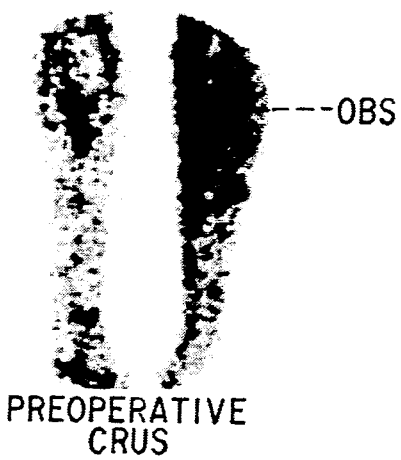
FIG. 8 is a scintigram showing increased uptake of $^{111}$In-labelled t-PA MoAb in the area of the arterial trifurcation proximal in the left crus before, and 1 and 40 hours after, an operation to remove an embolus in this area.
Figure 8B:
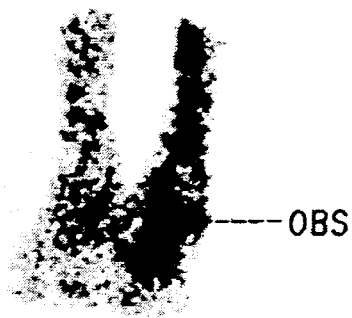
Figure 8C:
Figure 8D:
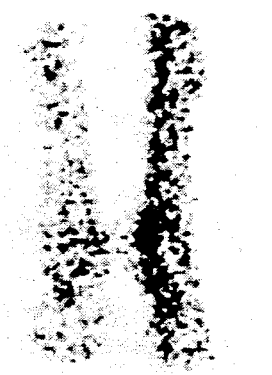

A 81 year-old man with an aneurism of the abdominal aorta covered with a mural thrombus was injected with the labelled antibody, and scintigraphic examination was begun 20 hours before the patient was operated for this condition. Increased fibrinolytic activity was observed at the site of the mural thrombus (FIG. 6). Samples of the blood vessel taken from this area during the operation showed a 60% higher uptake of the labelled antibody in the area of the mural thrombus relative to an aortic area with a high degree of arteriosclerosis but no thrombus formation.

Case "F"

A 69 year-old man was admitted to hospital because of respiratory problems. A combined perfusion and ventilation scintigram revealed small pulmonary emboli combined with a chromic obstructive lung disease. Scintigraphic examination 24 hours after injecting the labelled antibody showed an increased uptake of the antibody in the embolic area in the right lung (FIG. 7).

Case "G"

A 81 year-old woman who had a slight pain in the lower left leg for five days was admitted to hospital when the pain became severe and beginning hypoesthesia in the forefoot had been observed. An embolus in the crural region was diagnosed and removed by operation. Preoperative scintigraphic examination following injection of the labelled antibody showed an irregular increased uptake of the antibody in the area of the arterial trifurcation proximal in the left crus (FIG. 8). A diffuse increased activity in the forefoot was also observed indicating an increased local release of t-PA. Scintigraphic examination was continued postoperatively and a normalization was observed in the scintigram within 40 hours after the operation. The patient recovered without sequelae.

Case "H"

Figure 9:
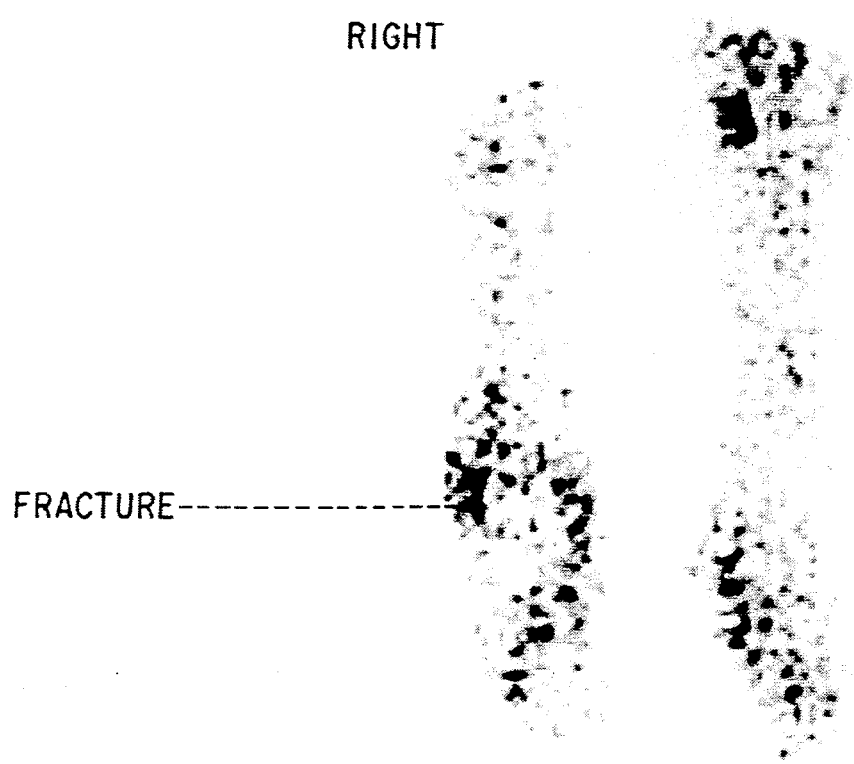
FIG. 9 is a scintigram showing increased uptake of $^{111}$In-labelled t-PA MoAb in the region of a lateral malleolar fracture.

An 81 year-old man was admitted to hospital with a lateral malleolar fracture in the right leg the day before injection of the labelled antibody. Scintigraphic examination showed an increased uptake of the antibody in the region of the fracture (FIG. 9).

Case "I"

Figure 10:
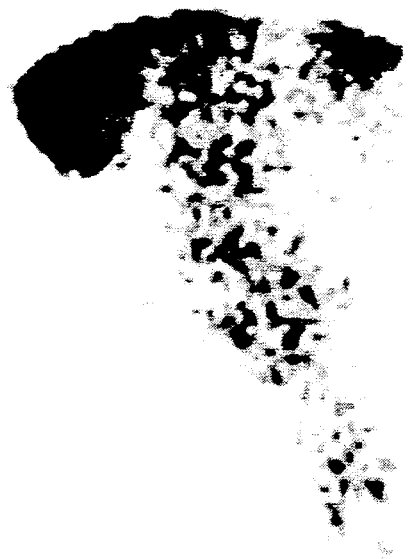
FIG. 10 is a scintigram of the abdominal region showing increased uptake of $^{111}$In-labelled t-PA MoAb in a thrombus of the left iliac vein.

A 32 year-old woman was admitted to hospital because of pronounced oedema of the left leg. Acute contrast phlebography revealed signs of a thrombosis of the left iliac vein. Scintigraphy 24 hours after injection of the labelled antibody showed high focal activity in the entire left iliac vein area (FIG. 10).

Case "J"

Figure 11:
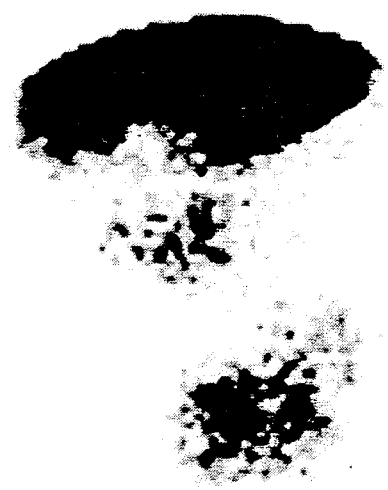
FIG. 11 is a scintigram of the abdominal region showing increased uptake of $^{111}$In-labelled t-PA MoAb in the bilateral ovarian region, the bladder and a tumormetastasis to the transverse colon.

A 72 year-old woman was admitted to hospital with a suspected malignant ovarian tumor. Ultrasound examination preoperatively revealed suspect changes of the right ovary and a 2×2×2 cm tumor mass in the upper abdominal region. Scintigraphy 24 hours after injection of the labelled antibody showed focal activity accumulation in the bladder, bilateral ovarian region and focally in the upper abdominal region (FIG. 11). During operation the ovarian cancer diagnosis was confirmed with bilateral ovarian cancer involving the bladder and with a distant metastasis to the transverse colon.

Case "K"

Figure 12:
FIG. 12 is a scintigram of the posterior abdominal region showing increased uptake of $^{111}$In-labelled t-PA MoAb in a periappendicular abscess.

A 38 year-old man was admitted to hospital because of fever and a slight pain located in the lower right part of the abdomen. Ultrasound examination revealed a focal homogeny mass in the lower right abdominal area consistent with a periappendicular abscess. A posterior view scintigram obtained 27 hours after injection of the labelled antibody showed focal activity accumulation in the same area indicating focal infection, which supported the ultrasound finding (FIG. 12).

Case "L"

A 60 year-old man with severe rheumatoid arthritis for several years was admitted to hospital because of a relapse of the disease. Scintigraphy 24 hours after injection of the labelled antibody showed increased activity in the joints involved in the acute state of the disease (FIG. 13).

Discussion

Figure 14:
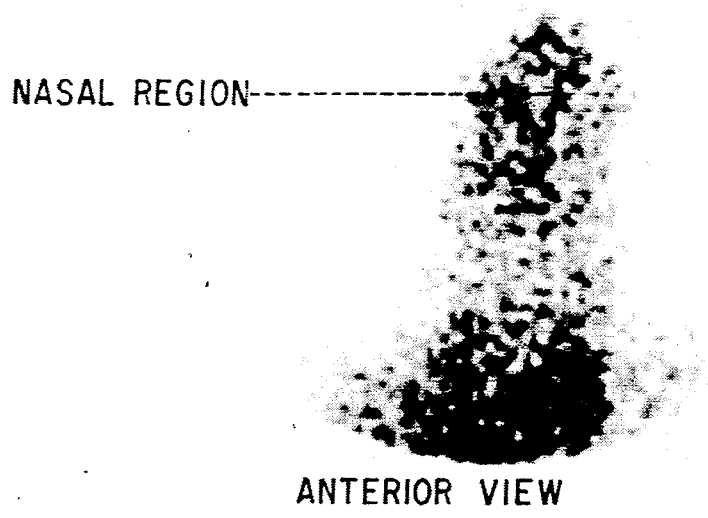
FIG. 14 is a scintigram showing increased uptake of $^{111}$In-labelled t-PA MoAb in the nasal region (the nasal mucosa generally exhibits increased fibrinolytic activity as do the prostate and gonads).

The results presented in the examples above indicate that the radiolabelled anti-t-PA MoAb may be used for diagnosing a wide variety of conditions associated with increased fibrinolytic activity in many different parts of the body, with the possible exception of tissues with a high intrinsic fibrinolytic activity such as the prostate, gonads and nasal mucosa (cf. FIG. 14). The MoAb exhibits a high immunospecificity and sensitivity. The uptake of the antibody in the liver was low for the first 4 hours which means that, contrary to the use of radiolabelled t-PA itself, hepatic extraction, and consequently a high local concentration of radioactivity in the liver, does not appear to be a problem. For the first few minutes after injection of the antibody, uptake in the thrombotic area was pronounced after which the background activity increased for up to several hours. The target/blood ratio then improved to give a clear scintigraphic image of the area of increased fibrinolytic activity.

EXAMPLE 3

Biological Background Subtraction—Animal Study a. Monoclonal Antibody

A monoclonal antibody was prepared as described in Example 1. The F(ab)$_2$ fragment was radiolabelled with $^{111}$In as described in Example 1.

The radiochemical purity of the labelled antibody was 93% as determined by HPLC.

The immunochemical purity of the labelled antibody was determined as the percentage of antibody radioactivity capable of binding to a t-PA coupled Sephgarose ® (Pharmacia AB, Sweden) column. The immunochemical purity of the conjugate was less than the radiochemical purity since some of the labelled antibody was immunological by non-reactive. The immunological purity of the antibody was 91%.

b. t-PA

The t-PA used in the experiments was Actilyse ® obtained from Boehringer Ingelheim.

c. Experimental Design

Two rabbits were injected intravenously with the antibody in dose/kg and specific radioactivity comparable to the human studies mentioned in Example 2.

Rabbit 1 received antibody at t=0 minutes. No t-PA was subsequently administered. Rabbit 2 received antibody at t=0 minutes. At t=120 minutes rabbit 2 received an intravenous injection of t-PA administered over a period of 1 minute. The injected amount of t-PA was in 3×molar concentration of the administered antibody.

d. Plasma Activity

Blood samples were taken at t=0, 10, 20, 40, 60 min and 2, 4, 6, 12, and 24 hours after the antibody injection. In rabbit 2 additional samples were taken 5, 10, 20, 40, and 60 min after the injection of t-PA.

Figure 15:
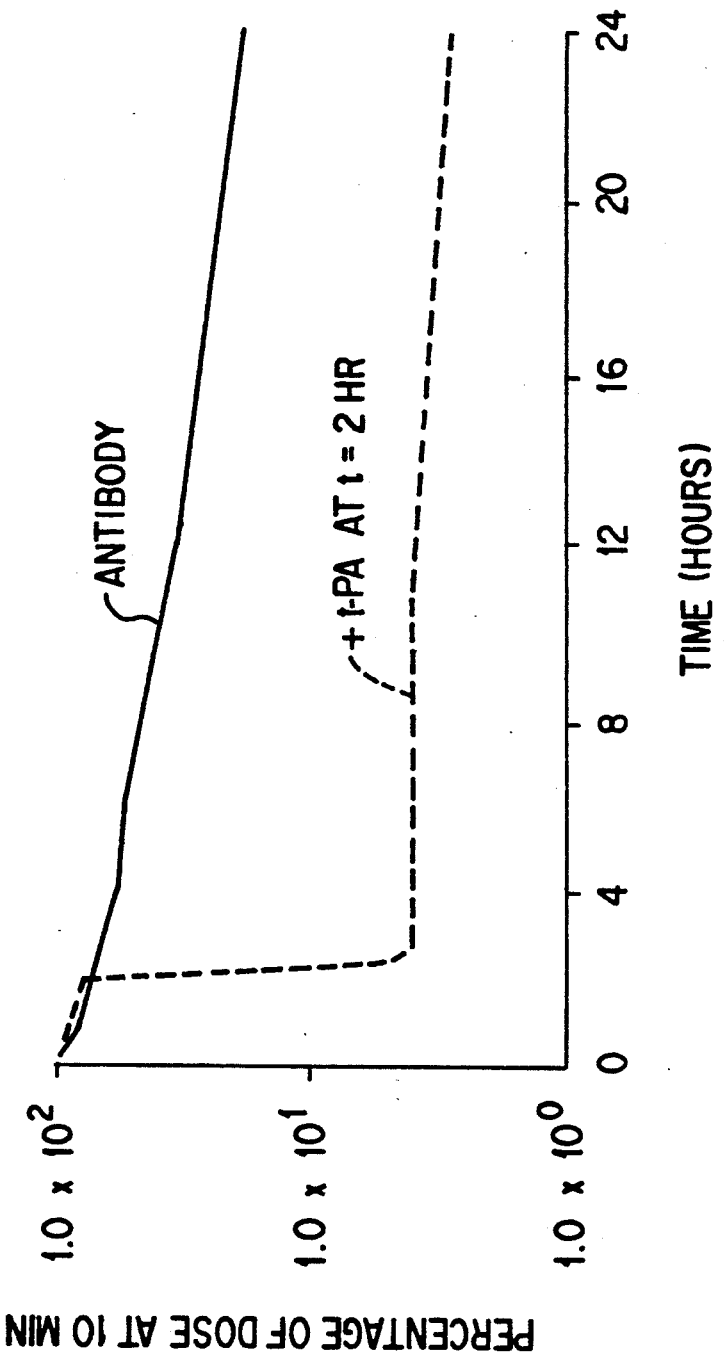
FIG. 15 is a graph showing the total radioactivity in plasma of the $^{111}$In-labelled t-PA MoAb with and without subsequent injection of t-PA.

For each sample, whole plasma activity was counted, and by regression analysis (Freelance Plus ver 3.01 ®) these data were adjusted to an exponential curve and the overall biological half-life was calculated. All curved presented were corrected for physical decay. The results are shown in FIG. 15.

$T_{\frac{1}{2}}$ of the antibody was 10.3 h.

When t-PA was added at t=2 hours a dramatic decrease in plasma activity was observed. Within 10 min a 92% reduction was observed.

Figure 16:
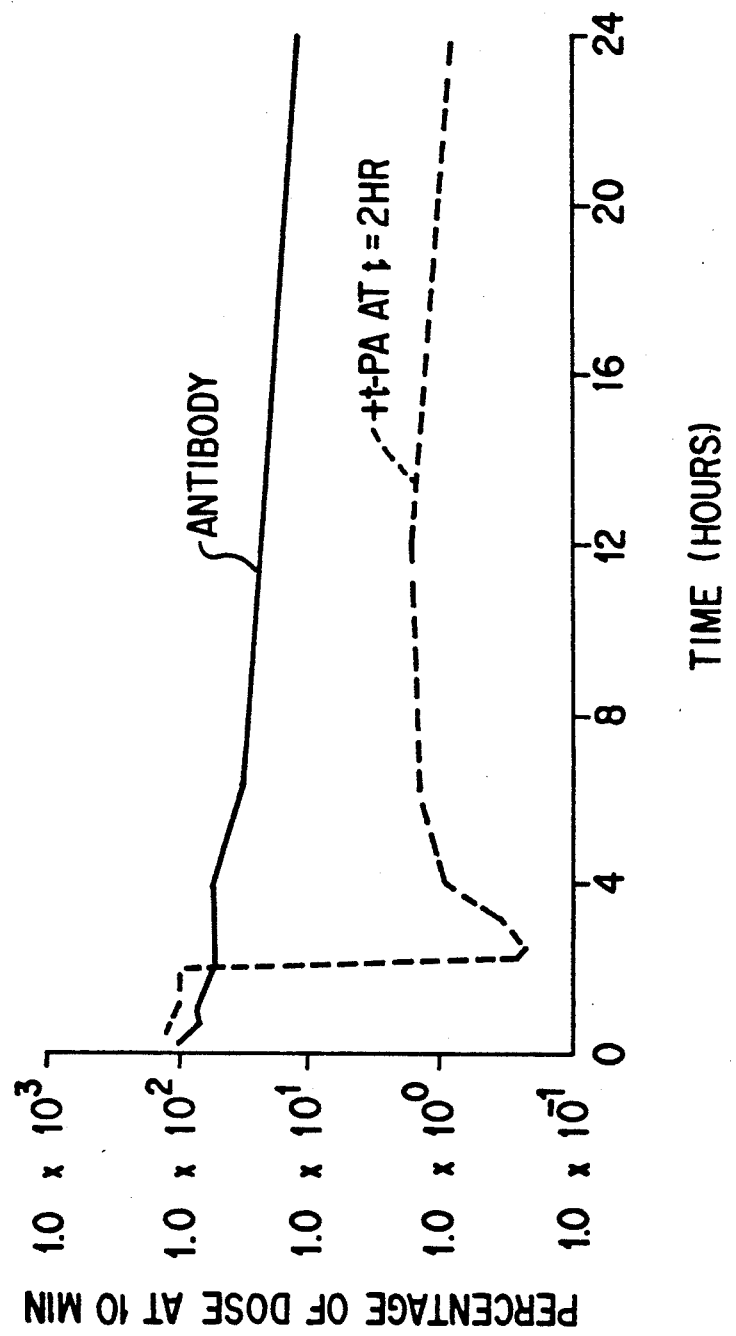
FIG. 16 is a graph showing the immunoreactive part of the $^{111}$In-labelled t-PA MoAb with and without subsequent injection of t-PA.

The biological half-life of the radiolabelled immunoreactive antibody in the plasmid was determined as the half-life was determined as the half-life of t-PA binding activity. The results are shown in FIG. 16.

Within 10 minutes after the injection of t-PA at t=2 hours more than 99% of the immunoreactive antibody activity was eliminated from the plasma. The half-like of this elimination is 1 minute. A slight increase in activity—up to 1.6%—is seen in the hours after the initial elimination. This is undoubtedly caused by redistribution of the extravascular antibody pool.

e. Whole Body Activity

Figure 17A:
FIG. 17 is a scintigram showing the organ distribution in rabbits of the $^{111}$In-labelled t-PA MoAb alone and complexed with t-PA.
Figure 17B:
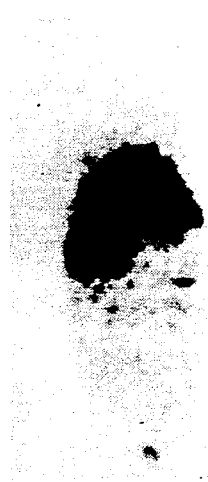

After 24 hours the rabbits were sacrificed. Whole body scintigrams of the rabbits were obtained. The results are shown in FIG. 17. Antibody not complexed with t-PA was mainly located in the kidneys, whereas antibody complexed with t-PA was almost exclusively found in the liver.

It appears from these experiments that t-PA/anti-t-PA MoAb complexes have a substantially shorter half-life in the organism than anti-t-PA alone. Furthermore, the experiments show that is possible to exploit the rapid t-PA/anti-t-PA MoAb clearance in vivo. The results of the study suggest that the hepatic t-PA receptor is responsible for this increase in antibody clearance.

The decline in total radioactivity is an essential parameter for imaging, in that the total plasma activity will decide the target/blood ratio. The reduction in t-PA binding radioactivity is a measure for the in vivo efficiency of the receptor elimination pathway. The decrease in total radioactivity will be less than the reduction in t-PA binding radioactivity unless the conjugate is 100% immunochemically active.

Example 4
Biological Background Subtraction—Human Study

A 77 year-old woman was admitted to hospital because of pronounced oedema of the right leg. An acute contrast phlebography exposed signs of a thrombosis in one of the lateral crural veins of the right leg. Scintigraphy was performed using a radiolabelled monoclonal antibody prepared as described in example 1. The radiochemical purity was only 67%.

One hour after injection of the radiolabelled antibody 5 mg of t-PA (Actilyse ® Boehringer Ingelheim) was injected.

a. Plasma Activity

Figure 18:
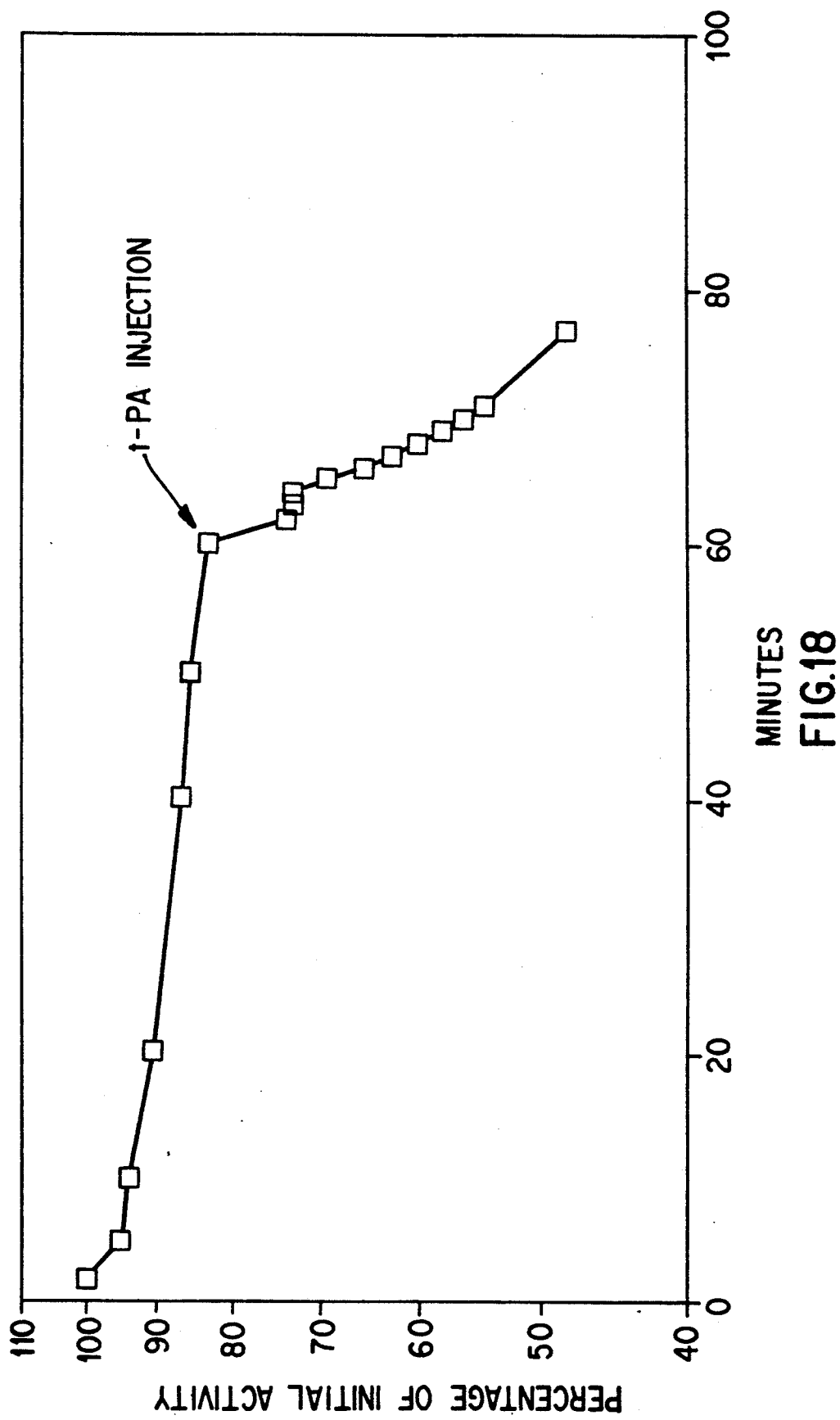
FIG. 18 is a graph showing the total radioactivity in human plasma of the $^{111}$In-labelled t-PA MoAb before and after injection of t-PA.

Blood samples were taken at regular intervals after the t-PA injection. For each sample, whole plasma radioactivity was counted in a well gamma-counter and plotted against time (FIG. 18). Exponential regression analysis was performed on Freelance Plus ver 3.01 ®. $T_{\frac{1}{2}}$ of the initial phase was 4.8 h. After t-PA injection, a substantial decrease in plasma activity was observed. Within 17 min, 50% reduction was observed.

b. Scintigraphy i) Biodistribution

Figure 19:
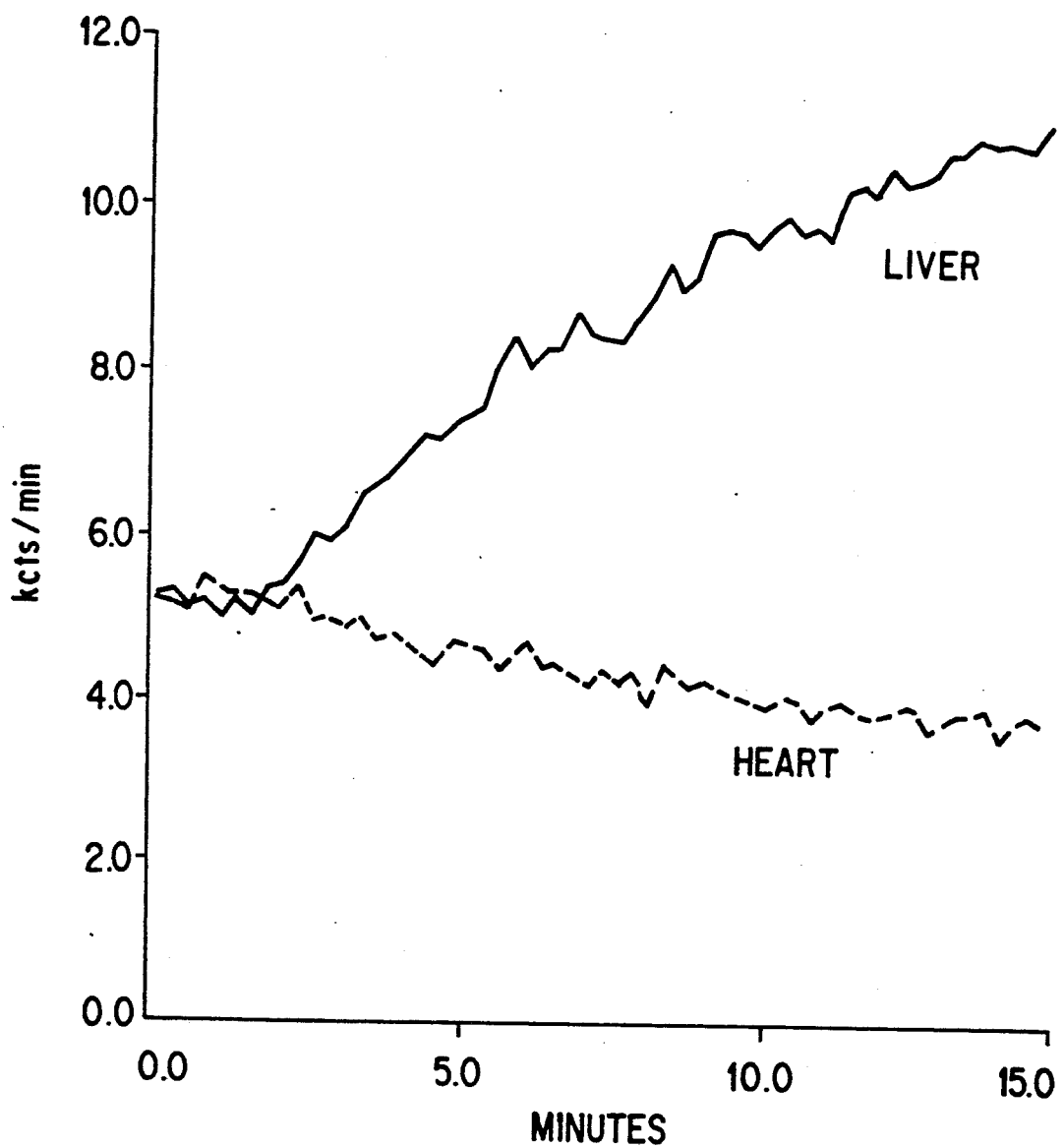
FIG. 19 is a graph showing the change in human organ distribution of the $^{111}$In-labelled t-PA MoAb following injection of t-PA.

During t-PA injection a dynamic acquisition of the liver and heart region was performed on the gamma-camera with 60 frames lasting 15 sec each. Activity of the blood (heart region) and the liver were calculated and plotted against time. The shift in distribution from circulating blood activity to bound liver activity following injection is clearly demonstrated on FIG. 19.

ii) Thrombus detection

Figure 20A:
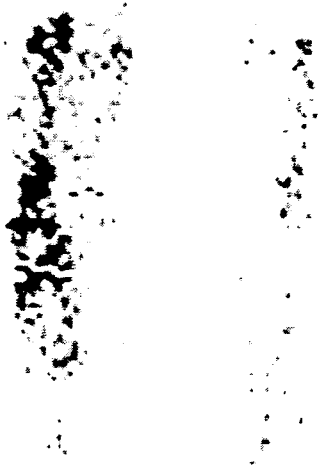
FIG. 20 is two scintigrams of the crural region initially showing increased accumulation of the $^{111}$In-labelled t-PA MoAb in the vascular bed of the right leg (A), and after t-PA injection revealing the focal thrombus area (top of the right leg) (B).
Figure 20B:
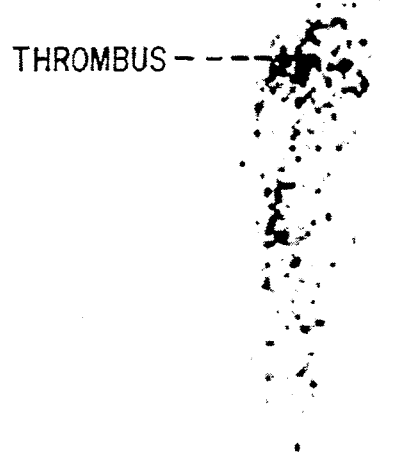

Initially, signs of stasis in the lower leg were revealed. However, the precise location of the thrombus could not be detected. After the t-PA injection, the activity in the dilated vascular bed diminished, and the thrombus area was detected (FIG. 20).

The biological background subtraction appears to improve the imaging technique, making it possible to detect thrombosis within a few hours.

All references cited herein are fully incorporated herein by reference. Having now fully described the invention, it will be understood by those with skill in the art that the scope may be performed within a wide and equivalent range of conditions, parameters and the like, without affecting the spirit or scope of the invention or any embodiment thereof.

What is claimed is:

1. A method of in vivo detection of increased release of a fibrinolytic enzyme or increased fibrinolytic activity in the human or animal body, the method comprising
   (a) administering, to a human or animal subject, a diagnostically effective amount of an antibody reactive with a fibrinolytic enzyme, or a fragment of said antibody, labelled with a substance permitting the detection in vivo of binding of the antibody or fragment thereof to the fibrinolytic enzyme, and
   (b) localizing increased release of a fibrinolytic enzyme or increased fibrinolytic activity in the subject by determining the presence of bound labelled antibody.

2. A method according to claim 1, wherein the antibody is a monospecific antibody or a fragment thereof.

3. A method according to claim 1, wherein the fibrinolytic enzyme is selected from the group consisting of tissue plasminogen activator (t-PA), plasmin, plasminogen, or an analogue thereof, or a modified fibrinolytic enzyme with affinity for fibrin.

4. A method according to claim 3, wherein the fibrinolytic enzyme is t-PA or an analogue thereof.

5. A method according to claim 4, wherein the fibrinolytic enzyme is native t-PA.

6. A method according to claim 1, wherein the antibody is a monoclonal antibody or a fragment thereof.

7. A method according to claim 6, wherein the monoclonal antibody is one reactive with t-PA or an analogue thereof.

8. A method according to claim 1, wherein the substance used to label the antibody is a radioactive isotope.

9. A method according to claim 8, wherein the radioactive isotope is selected from the group consisting of $^{111}$In, $^{99m}$Tc, $^{131}$I, $^{123}$I and $^{125}$I.

10. A method according to any of claims 1–9, wherein the antibody is administered in the form of a parenteral, nasal, enteral or rectal formulation, such as an injectable formulation, aerosol formulation, suspension, or enema.

11. A method according to any of claims 1–9, wherein a fibrinolytic enzyme is administered to the patient prior to or after step (a) of the method of claim 1.

12. A method according to claim 11, wherein the antibody is administered in the form of a parenteral, nasal, enteral or rectal formulation, such as an injectable formulation, aerosol formulation, suspension, or enema.

13. A method according to claim 11, wherein the increased fibrinolytic activity to be detected is associated with thrombosis, deep venous thrombosis, coronary thrombosis, cerebral thrombosis, cardiac thrombosis, mural thrombosis, gastrointestinal thrombosis, artherial thrombosis, embolism, pulmonary embolism, hemorrhage, cerebral hemorrhage, post-operative hemorrhage, gastrointestinal hemorrhage, hematuria, hemoptysis, gastric or duodenal ulcers, ischemia, neoplasms, breast cancer, ovarian cancer, malignant melanoma, brain or bone tumors, vasculitis, local infections, local inflammatory conditions, arthritis or fractures.

14. A method according to claim 11, wherein the fibrinolytic enzyme is selected from the group consisting of tissue plasminogen activator (t-PA), plasmin, plasminogen, or an analogue thereof, or a modified fibrinolytic enzyme with affinity for fibrin.

15. A method according to claim 14, wherein the antibody is administered in the form of a parenteral, nasal, enteral or rectal formulation, such as an injectable formulation, aerosol formulation, suspension, or enema.

16. A method according to claim 14, wherein the increased fibrinolytic activity to be detected is associated with thrombosis, deep venous thrombosis, coronary thrombosis, cerebral thrombosis, cardiac thrombosis, mural thrombosis, gastrointestinal thrombosis, artherial thrombosis, embolism, pulmonary embolism, hemorrhage, cerebral hemorrhage, post-operative hemorrhage, gastrointestinal hemorrhage, hematuria, hemoptysis, gastric or duodenal ulcers, ischemia, neoplasms, breast cancer, ovarian cancer, malignant melanoma, brain or bone tumors, vasculitis, local infections, local inflammatory conditions, arthritis or fractures.

17. A method according to any claims 1-9, wherein the increased fibrinolytic activity to be detected is associated with thrombosis, deep venous thrombosis, coronary thrombosis, cerebral thrombosis, cardiac thrombosis, mural thrombosis, gastrointestinal thrombosis, artherial thrombosis, embolism, pulmonary embolism, hemorrhage, cerebral hemorrhage, post-operative hemorrhage, gastrointestinal hemorrhage, hematuria, hemoptysis, gastric or duodenal ulcers, ischemia, neoplasms, breast cancer, ovarian cancer, malignant melanoma, or brain or bone tumours, vasculitis, local infections, local inflammatory conditions, arthritis or fractures.

* * * * *